United States Patent [19]

Sauer et al.

[11] Patent Number: 5,394,871
[45] Date of Patent: Mar. 7, 1995

[54] MEDICAL DIAGNOSTICS INSTALLATION

[75] Inventors: Roland Sauer, Nuernberg; Rudolf Brendl, Erlangen; Wolfgang Jaeger, Neunkirchen; Wolfgang Zerl, Herzogenaurach; Alois Noettling, Pottenstein; Hans-Peter Rieger, Nuernberg; Gerd Wessels, Erlangen, all of Germany

[73] Assignee: Siemens Aktiengesellschaft, Munich, Germany

[21] Appl. No.: 80,205

[22] Filed: Jun. 23, 1993

[30] Foreign Application Priority Data

Jun. 25, 1992 [EP] European Pat. Off. ............ 92110748
Jun. 25, 1992 [DE] Germany ................. 42 20 923.4

[51] Int. Cl.⁶ .................. A61B 5/00; A61B 8/00
[52] U.S. Cl. .................. 128/630; 128/660.01; 128/653.1
[58] Field of Search ............ 128/630, 660.01, 662.03, 128/660.07, 653.1; 378/92, 98

[56] References Cited

U.S. PATENT DOCUMENTS

| 4,553,254 | 11/1985 | Bach et al. ............... 378/98 |
| 4,974,248 | 11/1990 | Eils et al. ............... 378/98 |
| 5,018,178 | 5/1991 | Katsumata ............... 378/91 |
| 5,161,535 | 11/1992 | Short et al. ............ 128/660.01 |
| 5,233,517 | 8/1993 | Jindra ................. 128/654 X |
| 5,255,682 | 10/1993 | Pawluskiewicz et al. ..... 128/662.03 |

FOREIGN PATENT DOCUMENTS 0201891 11/1986 European Pat. Off. .
3034933 4/1982 Germany .
3324537 2/1984 Germany .
3330116 5/1984 Germany .
2151890 7/1985 United Kingdom .
WO88/00789 1/1988 WIPO .

OTHER PUBLICATIONS

Siemens Sales Brochure, "Wirstchaftlich, flexbel, zukunftssicher: Sireskop 5", Order No. A19100-M10-15-A796-01, pp. 1-25.

Primary Examiner—Francis Jaworski
Attorney, Agent, or Firm—Hill, Steadman & Simpson

[57] ABSTRACT

A medical diagnostics installation comprises components for portraying an examination region on a monitor and includes an operating unit which is spatially spaced from the monitor and has a control unit, either a sensor field, a joystick or a key field, for acting on a data processor for controlling the components. The data processor includes a data store that contains data corresponding to different operating menus, and these menus are capable of being called in via the operating unit and are displayed on the monitor. At least one operating condition of the medical diagnostics installation can be produced by the operating unit and the operating menus correspond to the operating conditions being displayed on the monitor are only the operating functions required for this operating condition. The operating functions are controllable via a mark or cursor which is controlled by either the sensor field, joystick or key field.

12 Claims, 8 Drawing Sheets

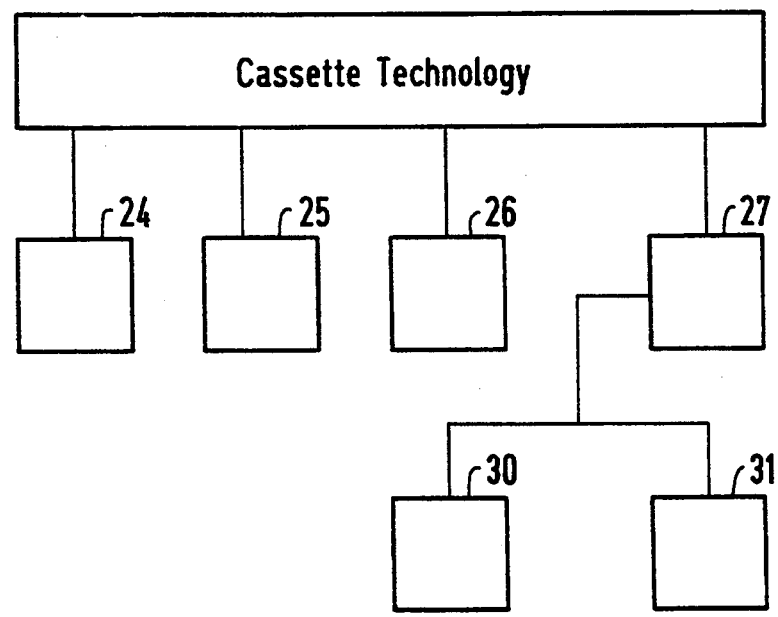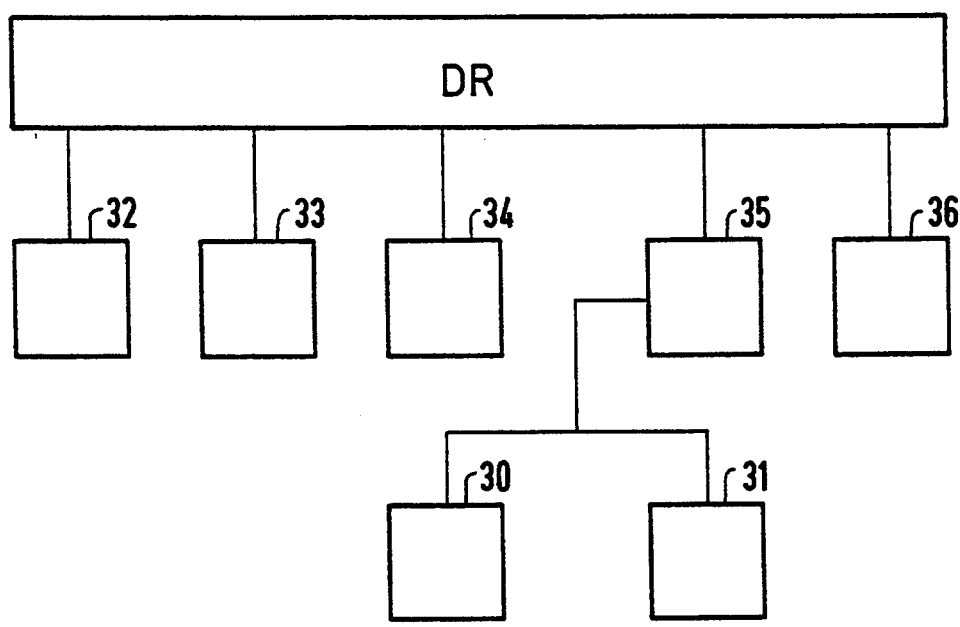
FIG 3

| spotfilm device | wall stand | second plane | tomographic device | table exposure |

Program: abdomen a.-p.                           Prof. Müller 80 kV

+3

50 mAs 285 ms

80%  100%

Quit    Store

FIG 8

| abdomen p.-a. | abdomen a.-p. | gallbladder a.-p. | gallbladder p.-a. | kidney survey | kidney R a.-p. | floating kidney |
|---|---|---|---|---|---|---|
| Program 7 | Program 8 | Program 9 | Program 10 | Program 11 | Program 12 | Program 13 |
| Program 14 | Program 15 | Program 16 | Program 17 | Program 18 | Program 19 | Program 20 |
| Program 21 | Program 22 | Program 23 | Program 24 | Program 25 | Program 26 | Program 27 |
| Program 28 | Program 29 | Program 30 | Program 31 | Program 32 | Program 33 | Program 34 |
| Program 35 | Program 36 | Program 37 | Program 38 | Program 39 | Program 40 | Program 41 |

Edit

FIG 9

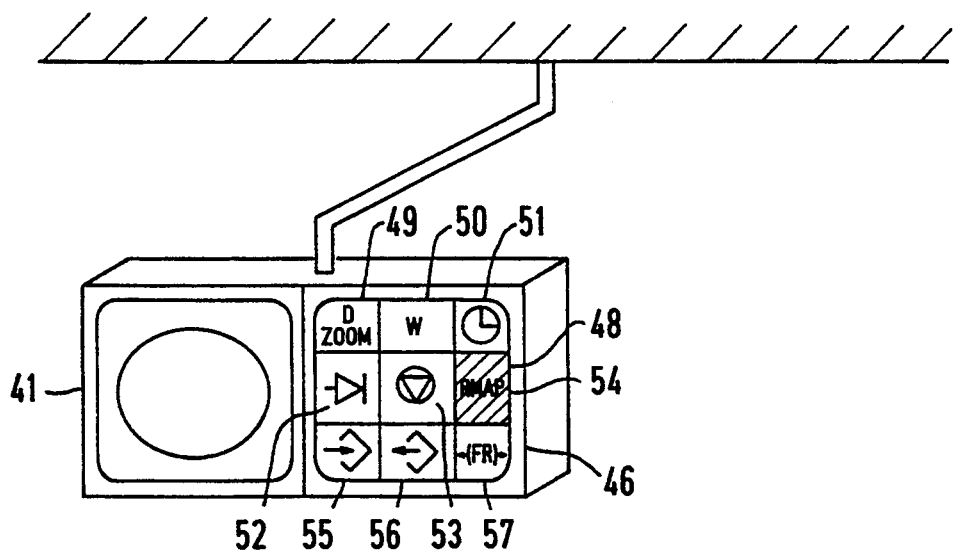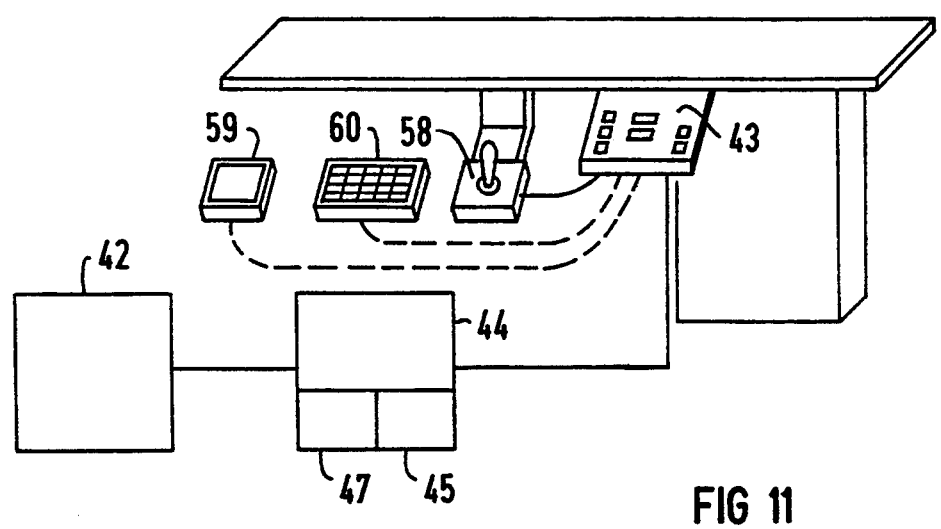
FIG 11

MEDICAL DIAGNOSTICS INSTALLATION

BACKGROUND OF THE INVENTION

The present invention is directed to a medical diagnostics installation having components for the portrayal of an examination region on a monitor, an operating unit spatially separated from the monitor which acts with a data processor for controlling the various components of the installation and has a data store allocated to the processor that contains data corresponding to different operating menus which can be selected through the operating unit and can be displayed on the monitor.

U.S. Pat. No. 4,553,254, whose disclosure is incorporated herein by reference thereto and which claims priority from German Published Application 30 34 933, discloses a medical diagnostics installation that is an x-ray diagnostics installation. The installation comprises an x-ray radiator having an x-ray generator, an x-ray device and auxiliary devices, a sheet film camera, an image intensifier video chain, as well as at least one control panel for the generator and device control as components. The control panel is provided with keys by which the parameters of the x-ray generator are set and the control of the x-ray device can be undertaken. To this end, the control panel is implemented as an intelligent data viewing means and is connected to a central data processor. The data processor controls the x-ray generator and the x-ray device and effects the reproduction of the data of the components on at least one data viewing means that can be called in from there. The control panel is provided with a picture screen on which a defined data program is reproduced with the assistance of the data processor as soon as the control panel is switched on. The reproduced data thereby appear at specific locations of the picture screen and can be inputted into the data processor by touching the picture screen at these locations. The data processor, in turn, correspondingly controls the x-ray device and x-ray generator or reproducing corresponding sub-programs. For example, the x-ray tube voltage and the x-ray tube current can be set and the dominant of the automatic exposure unit can be selected by touching the picture screen at predetermined locations. The operation of the x-ray diagnostics installation is simplified by selecting information sets in super-programs and sub-programs. The operation of the x-ray diagnostics installation by the picture screen presents problems insofar as the picture screen must then always be located within the reach of the examining person. Touching the picture screen leads to the contamination thereof, so that frequent cleaning is required. In addition, a control cannot be employed for hygienic reasons in the operating room.

Siemens' brochure "Sirescop 5", Order No. A19100-M1015-A796-01 discloses an x-ray diagnostics installation with which cassette exposures and transillumination exposures of an examination subject can be produced. All control elements for controlling the x-ray system are centrally accommodated in the target device control panel and in the guide handle.

As a consequence of the numerous control keys, it is necessary that the examining person become familiar with the topical arrangement of the individual control keys. For actuating the individual control keys, the operator must look away from the picture screen of the monitor on which the examination region is displayed and look at the control panel.

Medical diagnostics installations are known that enable an examination of an examination subject with ultrasound wherein an image of the examination subject can be displayed on a monitor and which can be controlled via control keys of a control panel.

SUMMARY OF THE INVENTION

It is an object of the present invention to provide a medical diagnostics installation of the above-mentioned types such that a simple and surveyable operation is possible.

This object is achieved by a medical diagnostics installation comprising components for displaying an examination region on a monitor, said components including an operating unit that is spatially separated from the monitor and which comprises means for acting on the data processor for controlling the components, a data memory or store is allocated to the data processor and contains data corresponding to different operating menus that can be called in by the data processor and can be displayed on the monitor, at least one operating condition of the medical diagnostics installation can be initiated by the operating unit, the operating menu corresponding to the operating condition is displayed on the monitor that will display only the operating functions required for this particular operating condition and, thus, the operating functions can be controlled by a mark or cursor which is controllable by the means for control which may include a joystick, a sensor field or a key field.

This object is likewise achieved by a medical diagnostics installation comprising components for displaying an examination region on a monitor, an operating unit that acts on a system controller for controlling the components, a data memory allocated to the system controller that contains data corresponding to different operating menus that can be called in via the operating unit and can be displayed on a separate display means neighboring the monitor, a mark or cursor generator allocated to the system controller for generating a mark or a cursor that can be displayed on the display means and is controllable by the operating unit, at least one operating condition of the medical diagnostics installation can be reproduced via the operating unit, whereby the operating menu corresponds to the operating condition being displayed on the display means that displays only the operating functions required for this operating condition, and that the operating functions are controllable via the control mark.

An advantage of the invention is that the medical diagnostics installation can be operated without the examining person having to look away from the monitor. The operation is simplified, since only a small number of operating elements are provided for control. Advantageously, the operating unit can comprise a joystick, a sensor field or a key field for controlling the mark or cursor. The medical diagnostics installation can, thus, be operated in a very uncomplicated way.

A medical diagnostics installation can be operated in an especially simple way when the operating menu corresponding to the preselected operating condition can be called in by touching a sensor field when the mark or cursor can be controlled by location-varying touching of the sensor field and when the operating function can be controlled by increased touching pressure as soon as the mark and the operating function are in coincidence with one another.

Other advantages and features of the invention will be readily apparent from the following description of the preferred embodiments, the drawings and claims.

BRIEF DESCRIPTION OF THE DRAWINGS

FIG. 3 is a diagrammatic illustration of the relationship of various operating menus of a medical diagnostics installation of FIG. 1;

FIG. 8 is a display on a monitor of an operating menu selected from the menu of FIG. 7;

FIG. 9 is a display of a menu of programs on a monitor which can be selected from the menu of FIG. 7;

FIG. 11 is a perspective view of a second exemplary embodiment of a medical diagnostics installation of the present invention.

DESCRIPTION OF THE PREFERRED EMBODIMENTS

Figure 1:
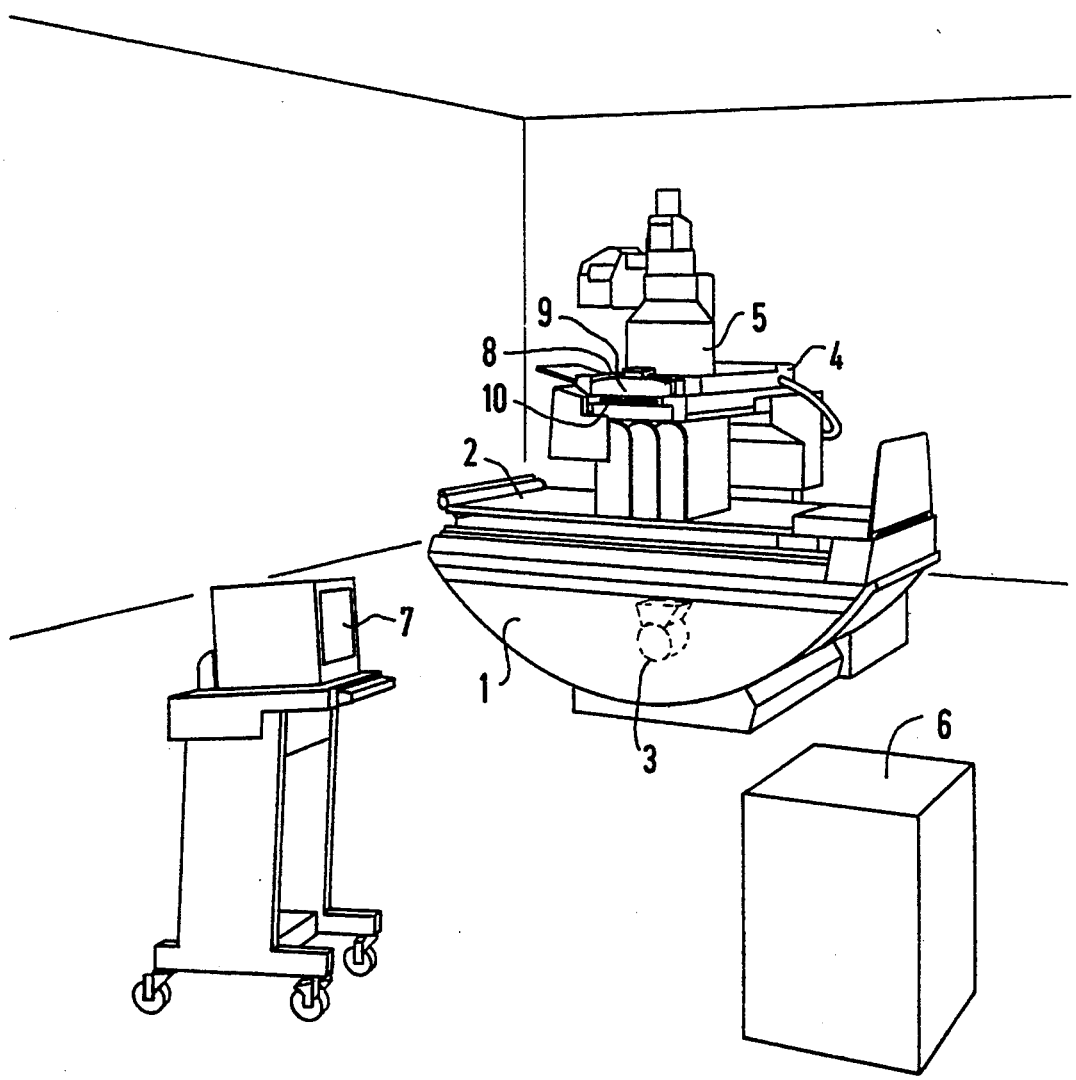
FIG. 1 is a perspective view of a first exemplary embodiment of a medical diagnostics installation of the present invention.

The principles of the present invention can be used in a medical diagnostics installation that is implemented as an x-ray diagnostics installation and illustrated in FIG. 1. The x-ray diagnostics installation includes a support plate 2 for the examination subject, which is adjustably supported by a supporting mechanism 1. An x-ray radiator 3 is arranged in the supporting mechanism 1 and includes an x-ray generator. A target device lies opposite the x-ray radiator 3 and the support plate 2 and is adjustably arranged and carries an x-ray image intensifier 5. The installation also includes a data processor 6 for controlling the components and for producing an image on a monitor 7 from the signals of the x-ray image intensifier 5. An adjustable grip 8 for the spatial adjustment of the target device 4, an operating unit 9 and a shaft or slot 10 for the acceptance of an x-ray film cassette are also provided in the target device 4.

Figure 2:
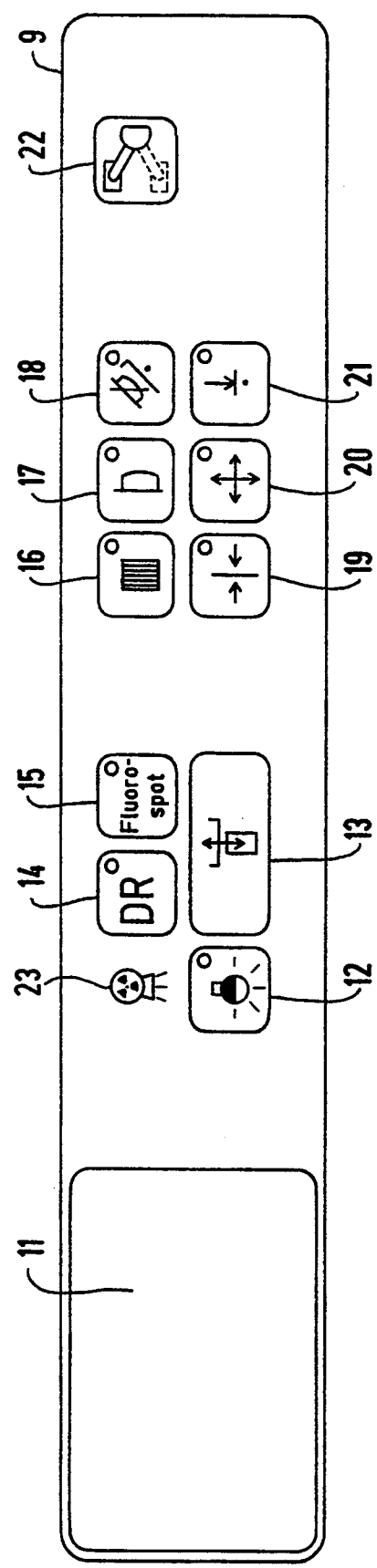
FIG. 2 is a plan view of an operating unit of the medical diagnostics installation of FIG. 1.

The operating unit 9, as illustrated, is locally separated from the monitor 7 and is shown in greater detail in FIG. 2. This operating unit 9 has a sensor field 11, and an extremely small number of function elements that, for example, are executed as control keys 12 through 22. The control keys 12 through 22 and the sensor field 11 act on the data processor 6 for controlling the various components. The control key 12, for example, serves the purpose of controlling room light. The control key 13 serves the purpose of opening the shaft or slot 10 so that an x-ray film cassette can be accepted or received therein. The control key 14 serves the purpose of selecting whether the digital radiography or an exposure in cassette technology is to be produced. The control key 15 serves the purpose of image documentation. The control key 16 serves the purpose of driving the grid. The control key 17 serves the purpose of tube control. The control key 18 serves the purpose of a myelography stop. The control key 19 serves the purpose of positioning the targeting device in a middle position. The control key 20 serves the purpose of arresting the targeting device in both the longitudinal and transverse directions. The control key 21 serves the purpose of arresting the compression tube. Finally, the control key 22 serves the purpose of turning the x-ray diagnostics installation on and off. A radiation monitoring display is indicated by reference 23.

Compared to the known x-ray diagnostics installation, the operating unit 9 comprises significantly fewer control keys so that a surveyable and simple operation is possible.

The operation of the x-ray diagnostics installation of the invention shall now be set forth in greater detail with reference to additional Figures. By actuating the control key 14, a predetermination can be made as to whether an exposure in cassette technology or whether a digital radiography is to be produced so that the corresponding operating conditions of the x-ray diagnostics installation is produced. In response thereto, the data processor 6 will produce an operating menu corresponding to the selected operating condition on the monitor 7 on the basis of the data in the data store. As already pointed out, the data corresponding to different operating menus corresponding to operating conditions are stored in the data store, and these are capable of being called in via the operating unit 9 and being displayed on the monitor 7.

Figure 4:
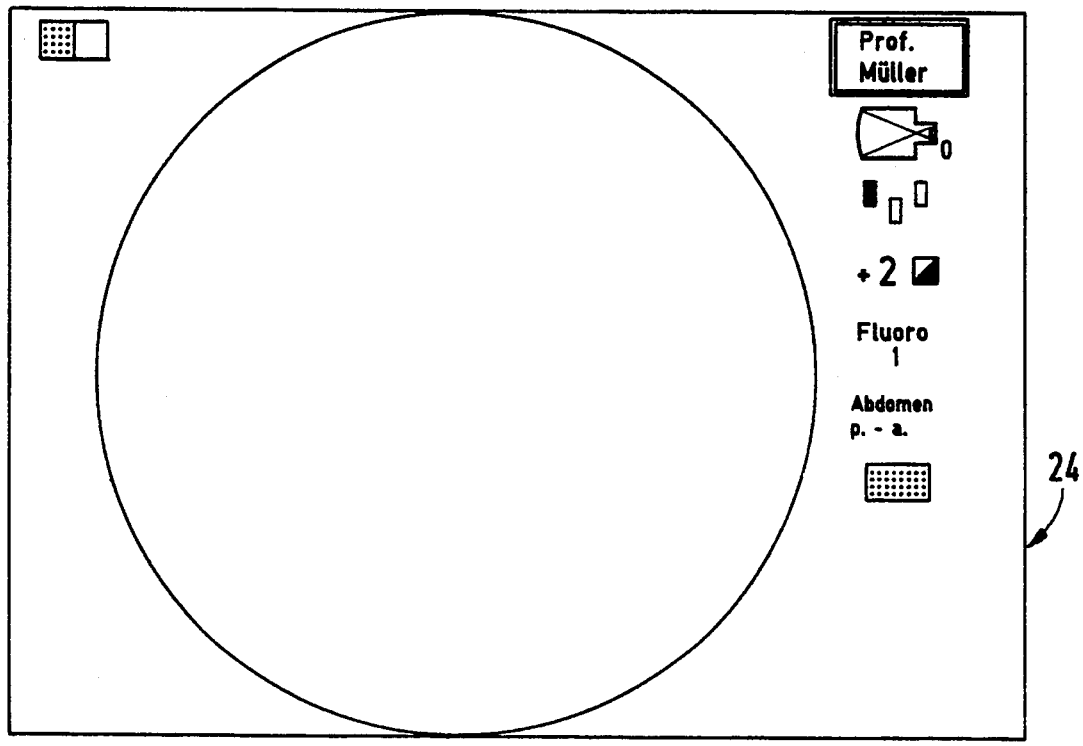
FIG. 4 is an illustration of the presentation on a monitor when a cassette technology is selected, transillumination is not carried out and the sensor field has not been touched.

FIG. 3 shows an example of the structure or relationship of the various operating menus for an x-ray diagnostics installation of the present invention. When the operating condition for cassette technology is selected with the control key 14, for example, the operating menu, generally indicated at 24 in FIG. 4, will be displayed on the monitor 7. This operating menu 24 appears when the cassette technology is selected, transillumination is not carried out and the sensor field 11 has not been touched. The current status of the x-ray diagnostics installation corresponding to the operating condition of the cassette technology as well as the potentially-provided control functions are displayed.

Figure 5:
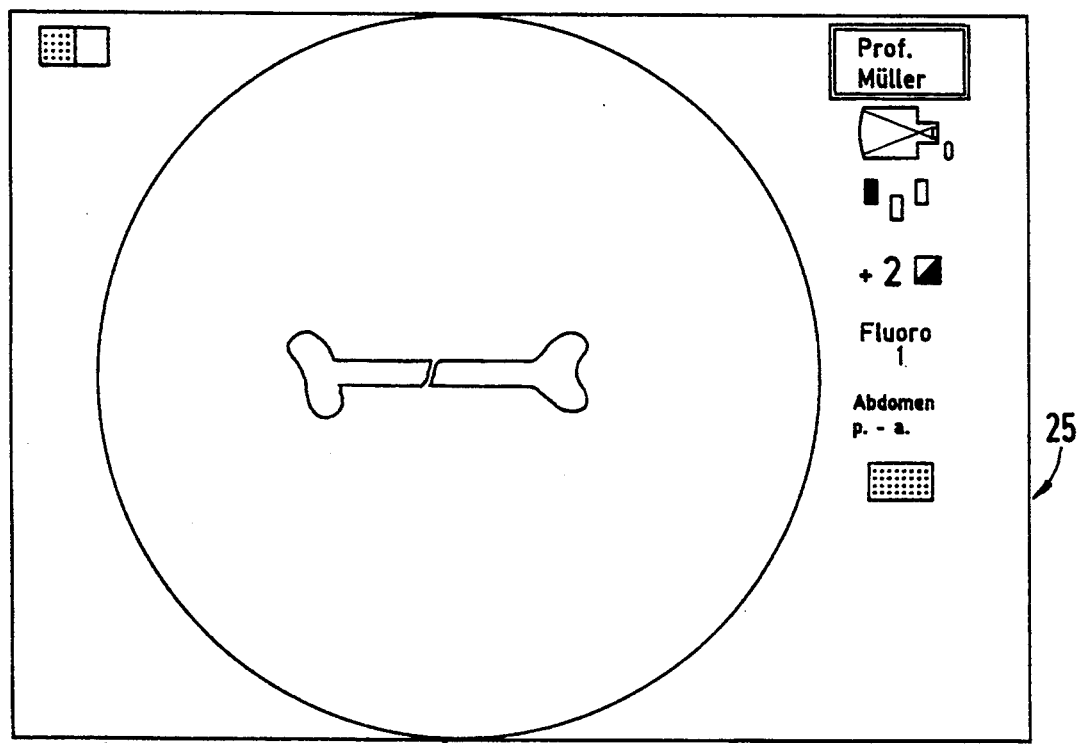
FIG. 5 is an illustration of the display on a monitor when the cassette technology is selected, transillumination of the subject occurs and the sensor field has not been touched.

When the operating condition of the cassette technology has been selected via the control key 14, a transillumination of an exposed subject occurs and the sensor field 11 is not touched, then the operating menu 25, which is illustrated in FIG. 5, will appear. In addition to the transillumination image, the current status of the x-ray diagnostics installation is also displayed.

Figure 6:
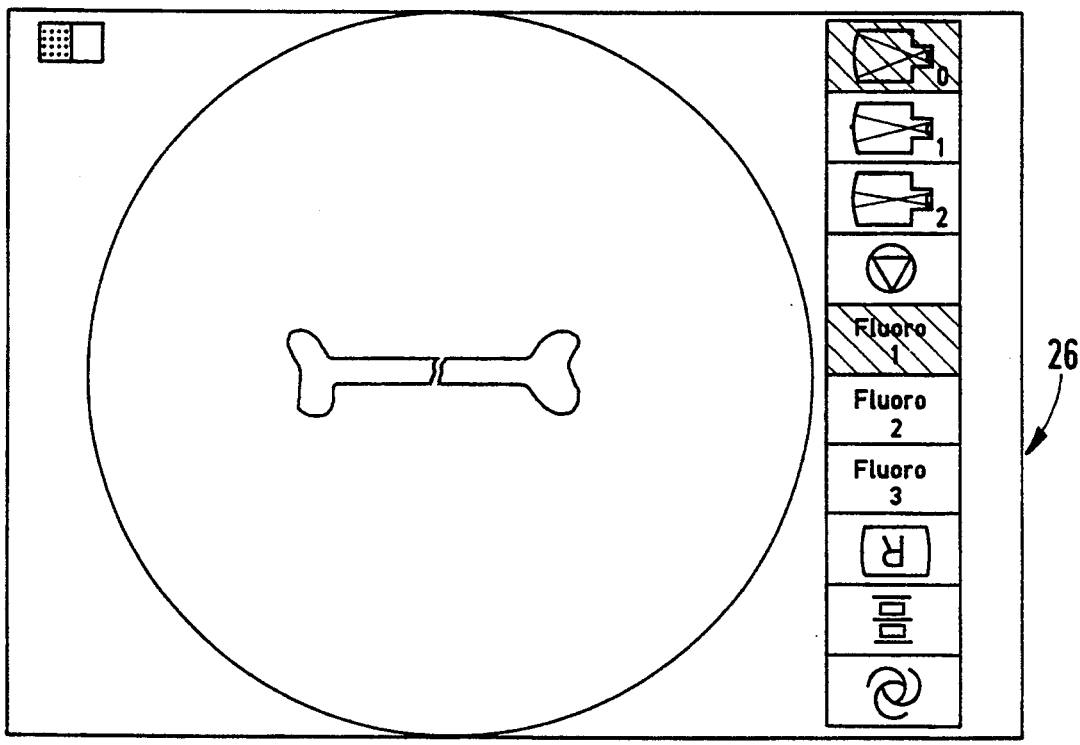
FIG. 6 is the display on a monitor when the cassette technology is selected, the subject is transilluminated and the sensor field has been touched.

The operating menu 26, shown in FIG. 6 as it appears on the monitor 7, will appear when the cassette technology has been selected with the control key 14, the exposure subject is transilluminated and the sensor field 11 has been touched. The fact that the sensor field 11 is touched may be seen from a mark or cursor which is controllable by the sensor field 11 and appears on the picture screen of the monitor 7. This mark will appear in the Figures as a shaded area.

Figure 7:
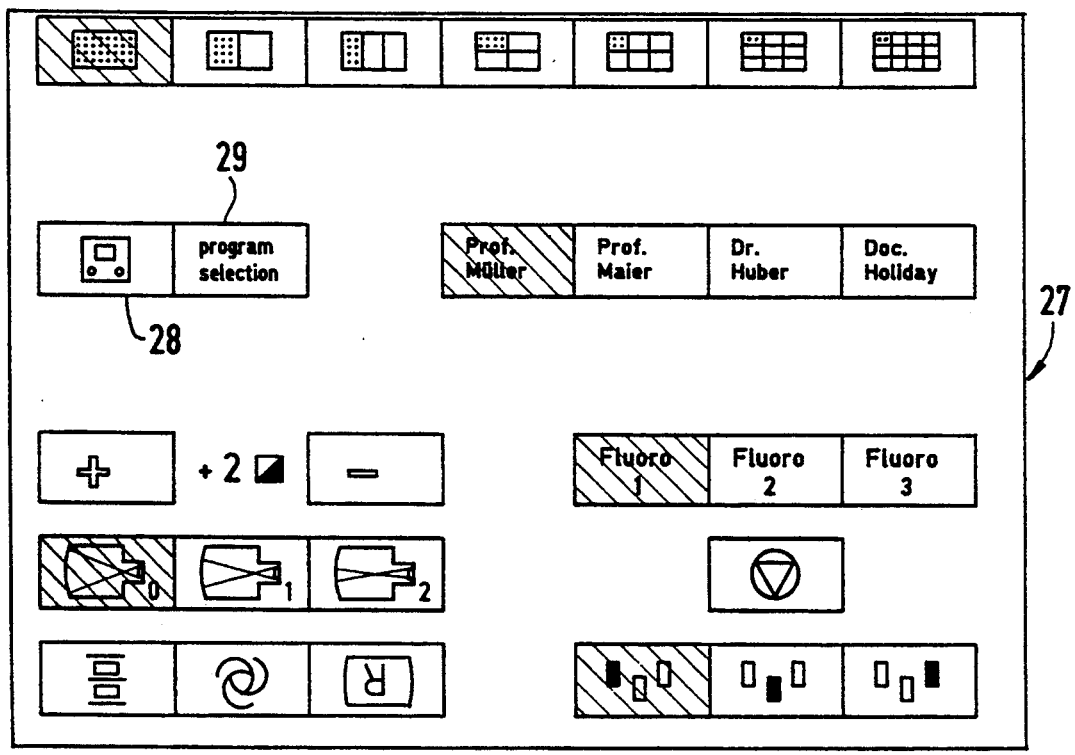
FIG. 7 is a the display when the cassette technology has been selected, transillumination has not been carried out and the sensor field has been touched.

When cassette technology is selected via the control key 14, transillumination has not yet been carried out and the sensor field 11 is touched, then the control menu, generally indicated at 27 in FIG. 7, will appear on the monitor 7. The entire picture of the monitor is, thus, utilized for this control menu.

For generating the mark, the data processor comprises a mark generator that is driven by the sensor field 11 so that the mark follows a topically-varying touching of the sensor field 11. The control function can be triggered by increasing touching pressure on the sensor field 11 when the mark and operating function are in coincidence with one another. The status display and potential switch and control functions appearing on the picture tube of the monitor 7 are to be considered operating or control functions.

When, for example, the parameter of the x-ray generators are to be varied, then the controllable mark is brought into coincidence with the control or operating function 28 and the operating menu 27 that corresponds to the x-ray generator being brought into coincidence therewith by topically varying touching of the sensor field 11. As a result, increased touching pressure on the sensor field 11, the operating menu, generally indicated at 30 in FIG. 8, will appear and the parameters of the x-ray generator are displayed therein as a current status. For example, the x-ray tube voltage can be displayed in this operating menu as a current status of 80 kV. When this status is to be changed, then the controllable mark is guided, for example, to neighboring operating function boxes identified with plus or, respectively, minus. When, for example, the controllable mark is in coincidence with the operating function box identified with a plus, then the x-ray tube voltage can be increased by increasing touch pressure on the sensor field 11. Conversely, the x-ray tube voltage can be reduced when the controllable mark coincides with the operating function box identified with a minus and an increased touching pressure on the sensor field 11 occurs. All operating or control functions shown in the operating menu can be triggered or, respectively, the status display can be changed in the same way.

When the controllable mark is guided onto the operating or control function box identified by reference numeral 29 in FIG. 7, then the operating menu generally indicated at 31 of FIG. 9 can be called in by increased touching pressure of the sensor field 11. The organ-specific programs of the x-ray diagnostics installation can be called in in this operating menu and, potentially, can be varied.

The operating menus 30 and 31 of FIGS. 8 and 9 are illustrated in FIG. 3 as being branched-off from the menu 27. The menus 24–27 are all branched from the cassette technology.

Figure 10:
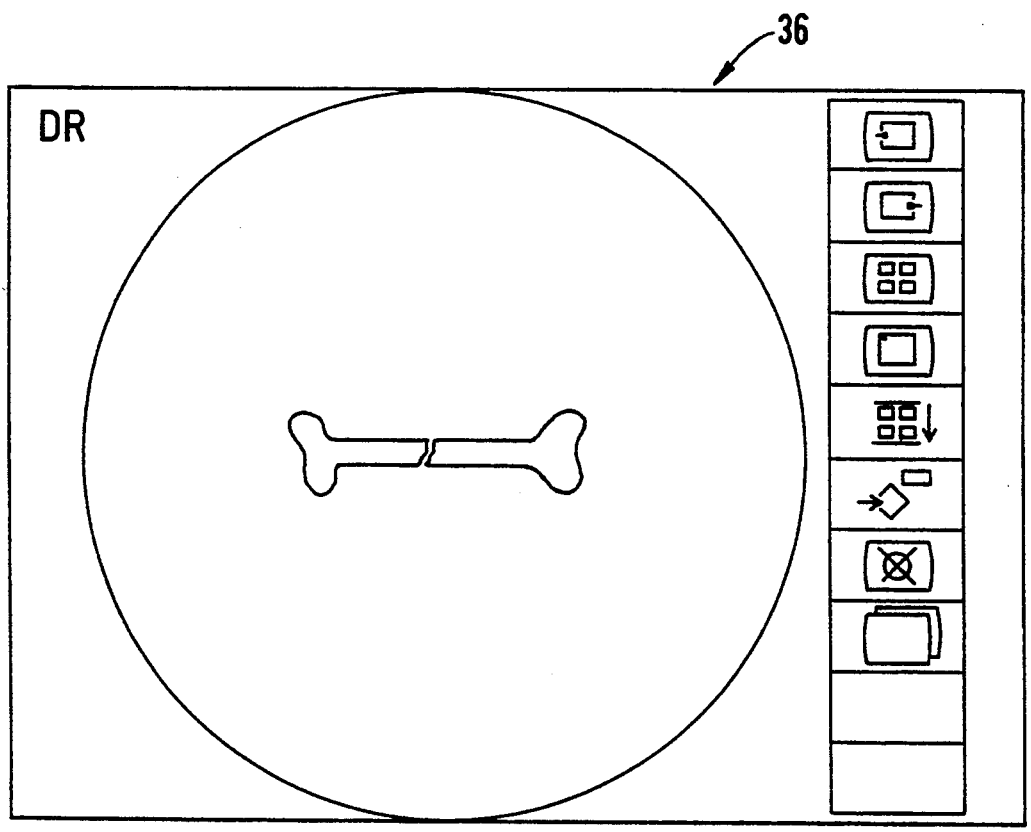
FIG. 10 is a display of a menu on the monitor for controlling image documentation.

When the operating condition of digital radiography is called in via the control key 14, then the operating menus can be called in that differ from the operating menus that are shown in FIGS. 6–9 in that only the status displays required for the digital radiography and, potentially, operating functions are mixed in on the picture screen of the monitor 7. These operating menus are referenced 30', 31' and 32–35 in FIG. 3. In addition, an additional operating menu, generally indicated at 36 in FIG. 10, in which the image documentation can be controlled will be displayed. The control of the x-ray diagnostics installation in this operating condition also occurs analogous to that set forth above via the mark controllable by the sensor 11.

The inventive fashioning of the x-ray diagnostics installation facilitates the operation whereof, for example, the physician examining a patient can control and operate the entire x-ray diagnostics installation without having to look away from the picture screen of the monitor 7 and essentially only by touching the sensor field 11. When operating the x-ray diagnostics installation, the physician, thus, need not concentrate on a multitude of control keys as required in the x-ray diagnostics installations of the prior art. The prompting for operating the x-ray diagnostics installation occurs automatically. The status displays and operating or control functions are automatically matched to the current operating condition and, thus, to the current examination technique by the operating menus, so that a complicated "leafing-through" the operating menus can be foregone. The selection of the control or operating elements, the operating or control functions and status displays corresponding to and required for the respective operating conditions, likewise, occur automatically.

FIG. 11 shows only those parts of another medical diagnostics installation of the invention that are critical to the invention, wherein the components for portraying an examination region on a monitor 41 are only symbolically shown and are referenced 42. When, as in the exemplary embodiment, the medical diagnostics installation is executed as an x-ray diagnostics installation, then at least one x-ray radiator having a means for gating the x-ray beam, an x-ray generator allocated to the x-ray radiator, a radiation receiver that, for example, receives the radiation penetrating through the examination subject as an image intensifier and converts it into electrical signals, and a video chain that produces an image of the examination region on the monitor 41 from these signals are provided as components.

In the second exemplary embodiment, the operating unit shown schematically is identified with the reference numeral 43 and acts on a system controller or data processor 44 for the purpose of controlling the components 42. The system controller 44 has a data store 45 provided therewith which contains data corresponding to different operating menus that can be called in via the operating unit 43 and can be displayed on a separate display means 46 adjacent to the monitor 41. A mark or cursor generator 47 is, likewise, allocated to the system controller 44. The mark or cursor generator 47 can generate a mark 48 on the display means 46 that is controllable by the operating unit 43. According to this invention, the operating condition of the medical diagnostics installation can be produced via the operating unit 43, whereby the operating menu corresponding to the operating condition is then displayed on the display 46. This operating menu only shows the operating functions required for this particular operating condition as a status display of the medical diagnostics installation and, potentially, switch and control functions. Exemplary operating functions are referenced 49 through 57. When the controllable mark 48 is displaced via the operating unit 43 onto the operating function referenced 52, and this is subsequently called in, for example by actuating a hardware key, then an operating menu wherein the parameters of the x-ray generator are, likewise, variable on the basis of the mark 48 controllable via the operating unit 43 appear on the display means 46.

The operating functions can be divided into at least two groups, wherein one group is to be ascribed to the general operation of the medical diagnostics installation, wherein, for example, an organ program is selected, the image frequency is varied, the diaphragm adjustment is undertaken, the components 42 are aligned onto the measuring field, the exposure mode and the x-ray parameters are set. The second group of operating functions controls the image system. For example, one can thereby leaf through scenes, can store images and, given digital image processing, subtraction and the road map can be activated or, respectively, deactivated.

According to the invention, the operating unit 43 can comprise a joystick 58 and/or a sensor field 59 and/or a key field 60 for controlling the mark or cursor 48. The mark is thereby also brought into coincidence with the operating function to be varied or triggered by swivelling the joystick 58 or by locationally changing touching of the sensor field 59 or, respectively, the key field 60. The operating function can be varied or triggered by actuating a hardware key in the case of the joystick 58 or by increasing touching pressure in the case of the sensor field 59 or key field 60.

It is possible within the framework of the present invention to also directly call in operating menus of the medical diagnostics installation by actuating a switch means specifically provided for this purpose, so that one need not "leaf through" operating menus. It is possible to control special apparatus functions, for example the diaphragm adjustment and alignment of the components, not only via operating functions of the operating menu but also on the basis of hardware functions given corresponding switch-over.

The operating unit 43, as well as the joystick 58, the sensor field 59 and the key field 60 can not only be arranged in the region of the patient support means or table, as shown in the exemplary embodiment, but can also have the possibility of being provided in a control room or as a mobile, displaceable unit in the examination room.

The display 46 can be implemented as a monitor, but can also be implemented as a display.

The medical diagnostics installation, however, can also be executed as an ultrasound diagnostics installation and then comprises an ultrasound and an image generating unit as components. The ultrasound applicator transmits ultrasound signals to an examination subject and receives ultrasound signals reflected therefrom. The received ultrasound signals are converted into electrical signals and are supplied to the image generating unit that produces an image of the examination region on the monitor on the basis of the receive signals. It is especially advantageous when the sensor field 59 is then provided at the ultrasound applicator, so that one-hand operation is possible.

One advantage of the medical diagnostics installation of the present invention is that a person examining a subject can control the medical diagnostics installation via the operating unit 43 and, in particular, via the joystick 58, the sensor field 59 or the key field 60 without having to look away from the monitor 41 that displays the examination region.

Although various minor modifications may be suggested by those versed in the art, it should be understood that we wish to embody within the scope of the patent granted hereon all such modifications as reasonably and properly come within the scope of our contribution to the art.

We claim:

1. A medical diagnostics installation comprising a monitor, components for portraying an examination region on the monitor, a data processor for controlling the components including a data store for containing data corresponding to different operating menus, an operating unit spatially separated from the monitor and having a sensor field, said operating unit having means for causing the data processor to display specific operating menus corresponding to an operating condition on said monitor, said operating menus displaying only operating functions required for a specific operating condition, and said monitor having a mark controllable by the sensor field for controlling specific operating functions on said monitor.

2. A medical diagnostics installation according to claim 1, wherein the operating unit is implemented as a control handle.

3. A medical diagnostics installation according to claim 1, wherein the components are executed as components of an x-ray diagnostics installation, said operating unit comprises function elements with which the operating condition of a cassette exposure and a digital radiography can be produced, wherein the corresponding operating menus and operating menus and visible images of the examination region and/or operating functions can be displayed in every operating condition on said monitor.

4. A medical diagnostics installation according to claim 1, wherein the components are executed as components of an ultrasound diagnostics installation.

5. A medical diagnostics installation comprising a monitor, components for portraying an examination region on the monitor, a data processor for controlling the components including a data store for containing data corresponding to different operating menus, an operating unit spatially separated from the monitor and having a sensor field, said operating unit having means for causing the data processor to display specific operating menus corresponding to an operating condition on said monitor, said operating menus displaying only operating functions required for a specific operating condition, and a mark controllable by the sensor field for controlling specific operating functions on said display, the operating menu corresponding to a preselected operating condition being called up by touching the sensor field wherein the mark is controllable by locally varying touching of the sensor field and the operating function being controllable by increasing the touching pressure as soon as the mark and operating function are in coincidence with one another.

6. A medical diagnostics installation comprising a monitor for portraying an examination region, components for portraying the examination region on said monitor, a system controller for controlling the components, an operating unit acting on the system controller, said system controller including a data store that contains data corresponding to different operating menus which can be called up via the operating unit and can be displayed on a separate display means adjacent to the monitor, a mark generator means allocated to the system controller for generating a controllable mark on the display means and controllable by the operating unit, at least one operating condition of the medical diagnostics installation being produced via the operating unit, an operating menu corresponding to the operating condition being displayed on the display means, said operating menu displaying only the operating functions required for this specific operating condition and the operating functions being controllable via the controllable mark.

7. A medical diagnostics installation according to claim 6, wherein the operating unit comprises a joystick for controlling the mark.

8. A medical diagnostics installation according to claim 6, wherein the operating unit comprises a sensor field for controlling the mark.

9. A medical diagnostics installation according to claim 6, wherein the operating unit comprises a key field for controlling the mark.

10. A medical diagnostics installation according to claim 6, wherein components are executed as components of an x-ray diagnostics installation, wherein the operating unit comprises a functional element with which the operating conditions of a cassette exposure or digital radiography can be produced and wherein the corresponding operating menus, operating menus and visual images of the examination region and of the operating functions can be displayed in every operating condition.

11. A medical diagnostics installation according to claim 6, wherein the components are executed as components of an ultrasound diagnostics installation.

12. A medical diagnostics installation according to claim 11, wherein the sensor field is arranged at the ultrasound applicator.

* * * * *